United States Patent [19]

Harrington, Jr.

[11] Patent Number: 5,340,805
[45] Date of Patent: Aug. 23, 1994

[54] DANAZOL FOR TREATMENT OF URINARY INCONTINENCE

[75] Inventor: William J. Harrington, Jr., Miami, Fla.

[73] Assignee: Sterling Winthrop Inc., New York, N.Y.

[21] Appl. No.: 990,395

[22] Filed: Dec. 10, 1992

[51] Int. Cl.$^5$ ............... A61K 31/58; A61K 31/56
[52] U.S. Cl. ................... 514/176; 514/177; 514/178
[58] Field of Search ............... 514/177, 178, 170, 176

[56] References Cited

U.S. PATENT DOCUMENTS

| | | | |
|---|---|---|---|
| 4,544,555 | 10/1985 | Gastaud | 514/178 |
| 4,908,358 | 3/1990 | Schreiber | 514/177 |
| 4,997,653 | 3/1991 | Igarsohi | 424/433 |

OTHER PUBLICATIONS

The Merck Index, Eleventh Edition, Merck & Co., Rahway, N.J., Monograph 2811, 1989.
Physicians Desk Reference ®, Forty-Sixth Edition, 1992, pp. 2046–2047.
William J. Harrington et al., AIDS Research and Human Retroviruses, vol. 7, No. 12, 1991, pp. 1031–1034.

*Primary Examiner*—Marianne M. Cintins
*Assistant Examiner*—T. J. Criares
*Attorney, Agent, or Firm*—Liza D. Hohenschutz

[57] ABSTRACT

The method of use of danazol for reducing or eliminating urinary incontinence and any associated frequent urination in a person suffering therefrom and pharmaceutical compositions therefor are disclosed.

8 Claims, No Drawings

DANAZOL FOR TREATMENT OF URINARY INCONTINENCE

BACKGROUND OF THE INVENTION

1. Field of the Invention

The invention relates to danazol or a pharmaceutical composition thereof for treatment of urinary incontinence and any associated frequent urination.

2. Information Disclosure Statement

The Merck Index (Eleventh Edition, Merck & Co., Rahway, N.J., 1989, monograph 2811) describes danazol under that name, which is the generic name, and by the chemical name 17α-pregn-4-en-20-yno[2,3-d]isoxazol-17-ol and sets forth the following information concerning biological properties and clinical utility thereof:

> Anterior pituitary supressant [sic]. Anabolic steroid derivative of ethisterone, q.v., with mild androgenic side effects (an impeded androgen). . . . Clinical studies in endometriosis . . . Use in idiopathic thrombocytopenic purpura . . . in hemophilia . . . THERAP CAT: Antigonadotropin.

Physician's Desk Reference ® (Forty-sixth Edition, 1992, pp. 2046–2047) describes danazol under the brand name DANOCRINE ®, which is a pharmaceutical composition of danazol in capsule form containing as active ingredient 50 milligrams, 100 milligrams or 200 milligrams of danazol per capsule and as inactive ingredients benzyl alcohol, gelatin, lactose, magnesium stearate, parabens, sodium propionate, starch and talc, with indication for use in endometriosis, fibrocystic breast disease and hereditary angioedema.

William J. Harrington, Jr. et al. (AIDS Research and Human Retroviruses, Volume 7, Number 12, 1991, pp. 1031–1034) describes resolution of urinary incontinence in two women having tropical spastic paraparesis or HTLV-1 associated myelopathy (TSP/HAM) by treatment with danazol. The issue of the journal containing the reference was mailed to subscribers on Dec. 18, 1991 by the publisher, Mary Ann Liebert, Inc., Publishers, 1651 Third Avenue, New York, N.Y. 10128. The first named author of the reference, William J. Harrington, Jr., is the presently named inventor, William Joseph Harrington, Jr.

Urinary incontinence and frequent urination are known secondary effects not only in persons having tropical spastic paraparesis or HTLV-1 associated myelopathy (TSP/HAM) but also in persons having spinal cord injury and multiple sclerosis. The invention is a medical advance in treating urinary incontinence and frequent urination.

SUMMARY OF THE INVENTION

In a process aspect the invention is the method of reducing or eliminating urinary incontinence and any associated frequent urination in a person suffering therefrom which comprises administering to the person an amount of 17α-pregn-4-en-20-yno[2,3-d]isoxazol-17-ol or a pharmaceutical composition thereof effective in reducing or eliminating the urinary incontinence and any associated frequent urination.

In a composition aspect the invention is a pharmaceutical composition of 17α-pregn-4-en-20-yno[2,3-d]isoxazol-17-ol for reducing or eliminating urinary incontinence and any associated frequent urination in a person suffering therefrom.

DETAILED DESCRIPTION OF THE INVENTION

As shown by the above-cited Merck Index and Physician's Desk Reference ® references danazol is a known chemical substance and a drug of commerce and is available by prescription. The pharmaceutical composition thereof of the invention is any composition wherein the active ingredient is danazol and the inactive ingredients are pharmaceutically acceptable and do not interfere with the purpose of reducing or eliminating urinary incontinence and any associated frequent urination in a person suffering therefrom. The composition can be prepared for oral, parenteral or rectal administration and can be in solid or liquid dosage form including capsules, tablets, suppositories, solutions, suspensions and emulsions. Conventional pharmaceutically acceptable vehicles and techniques are used in preparing these dosage forms. A composition for oral administration is preferred. The unit dosage is preferably in the form of a capsule or a tablet, most preferably a capsule. The amount of danazol in each unit dosage is such that a reasonable number of unit dosages per day, preferably from one to four, produce the effect of reducing or eliminating urinary incontinence and any associated frequent urination in a person suffering therefrom.

A pharmaceutical composition of the invention is packaged for sale or distribution in packages with instruction for use thereof for reducing or eliminating urinary incontinence and any associated frequent urination in a person suffering therefrom.

The capsules described by the above-cited Physician's Desk Reference ® reference and containing as active ingredient 50 milligrams, 100 milligrams or 200 milligrams of danazol per capsule and as inactive ingredients benzyl alcohol, gelatin, lactose, magnesium stearate, parabens, sodium propionate, starch and talc are suitable for carrying out the invention and were used in the following examples, wherein they are referred to simply as 200-milligram danazol capsules and wherein administration of one 200-milligram danazol capsule from one to three times daily to a person suffering from urinary incontinence and any associated frequent urination was found effective in reducing or eliminating the urinary incontinence and any associated frequent urination.

Each of the nine persons described in the following examples was diagnosed as having tropical spastic paraparesis or HTLV-1 associated myelopathy (TSP/HAM) whose primary effects are lower extremity weakness and spasticity.

EXAMPLE 1

A woman 44 years of age had disease of 15 years duration, weighed 92 pounds, and had frequent urination and incontinence together with the primary effects of her disease. Treatment with one 200-milligram danazol capsule three times daily was begun. After one month of treatment she had resolution of her urinary incontinence and painful abdominal and leg spasms and improvement in strength of her legs. After four or five months of treatment she had gained 20 pounds of weight and improvement in her ability to walk.

EXAMPLE 2

A woman 48 years of age who had frequent urinary incontinence was treated with one 200-milligram danazol capsule once daily. By the fourth week of treatment her urinary incontinence had resolved and her ability to walk had improved.

EXAMPLE 3

A woman 45 years of age who had frequent urinary incontinence and urinated from four to six times a night was treated with one 200-milligram danazol capsule three times daily. Within three weeks of treatment her urinary incontinence ceased. Her frequency of urination eventually decreased to once a night.

EXAMPLE 4

A woman 39 years of age who had severe urinary incontinence and awoke hourly at night to urinate was treated with one 200-milligram danazol capsule three times daily. By the eighth week of treatment her urinary incontinence had resolved. She eventually could sleep all night without having to urinate.

EXAMPLE 5

A woman 48 years of age who had frequent urinary incontinence which awakened her from six to eight times a night was treated with one 200-milligram danazol capsule three times daily. After three weeks of treatment her urinary incontinence ceased. Her nightly awakenings to urinate eventually decreased to two.

EXAMPLE 6

A woman 64 years of age who had frequent urinary incontinence and awoke five or six times a night to urinate was treated with one 200-milligram danazol capsule three times daily. Within three weeks of treatment her urinary incontinence ceased. Her frequency of urination eventually decreased to once a night.

EXAMPLE 7

A woman 69 years of age who had tropical spastic paraparesis or HTLV-1 associated myelopathy (TSP/HAM) and associated urinary incontinence and required post-void catheterization for 800 milliliters of residual urine was treated with one 200-milligram danazol capsule three times daily. After three weeks of treatment the residual urine decreased to 100–150 milliliters. Her urinary incontinence ceased.

EXAMPLE 8

A woman 26 years of age who had frequent urinary incontinence was treated with one 200-milligram danazol capsule three times daily. Within three weeks of treatment her urinary incontinence disappeared. She showed mild asymptomatic increases in liver enzymes. The danazol dose was decreased to one 200-milligram danazol capsule twice daily.

EXAMPLE 9

A woman 50 years of age who had polymyositis as well as tropical spastic paraparesis or HTLV-1 associated myelopathy (TSP/HAM) and associated frequent urinary incontinence and six nightly urinations was treated with prednisone (five milligrams every other day after three weeks) for the polymyositis and with one 200-milligram danazol capsule three times daily for the TSP/HAM. By the fourth week of treatment her urinary incontinence ceased and her nightly urinations decreased to two.

I claim:

1. The method of treating urinary incontinence and any associated frequent urination in a person suffering therefrom which comprises administering to the person an amount of 17α-pregn-4-en-20-yno[2,3-d]isoxazol-17-ol or pharmaceutical composition thereof effective in reducing or eliminating the urinary incontinence and any associated frequent urination.

2. The method according to claim 1 wherein the 17α-pregn-4-en-20-yno[2,3-d]isoxazol-17-ol is administered in a pharmaceutical composition.

3. The method according to claim 2 wherein the pharmaceutical composition is in the form of an oral unit dosage.

4. The method according to claim 3 wherein the oral unit dosage is a capsule containing as active ingredient from about 50 milligrams to about 200 milligrams of 17α-pregn-4-en-20-yno[2,3-d]isoxazol-17-ol.

5. The method according to claim 4 wherein the capsule contains as active ingredient 50 milligrams, 100 milligrams or 200 milligrams of 17α-pregn-4-en-20-yno[2,3-d]isoxazol-17-ol.

6. The method according to claim 5 wherein the capsule contains as active ingredient 200 milligrams of 17α-pregn-4-en-20-yno[2,3-d]isoxazol-17-ol.

7. The method according to claim 6 wherein the capsule is administered from one to four times daily.

8. The method according to claim 7 wherein the capsule is administered three times daily.

* * * * *